United States Patent [19]

Mendy et al.

[11] Patent Number: 5,780,439
[45] Date of Patent: Jul. 14, 1998

[54] WHEY PROTEIN HYDROLYSATES AND MIXTURES THEREOF WITH CASEIN AND/OR SOY PROTEIN HYDROLYSATES

[75] Inventors: Francois Mendy, Boulogne; Jean-Maurice Kahn, Berne; Loic Roger, Chantepie, all of France

[73] Assignee: Novartis Nutrition AG, Berne, Switzerland

[21] Appl. No.: 693,653

[22] Filed: Aug. 9, 1996

Related U.S. Application Data

[63] Continuation of Ser. No. 353,652, Dec. 9, 1994, abandoned, which is a continuation of Ser. No. 960,143, Oct. 13, 1992, abandoned, which is a continuation of Ser. No. 591,593, Oct. 2, 1990, abandoned.

[30] Foreign Application Priority Data

Oct. 2, 1989 [GB] United Kingdom ............. 8922181
Oct. 16, 1989 [GB] United Kingdom ............. 8923290

[51] Int. Cl.⁶ .................. A23C 21/02; A23C 21/04; A23C 21/06; A61K 38/01
[52] U.S. Cl. ............. 514/21; 426/583; 426/657; 426/804; 435/68.1; 530/343; 530/360; 530/365; 530/378; 530/407; 530/833
[58] Field of Search ............... 514/8.21; 435/68.1; 426/580, 583, 657, 804; 530/343, 360, 361, 365, 366, 378, 407, 833

[56] References Cited

U.S. PATENT DOCUMENTS

| | | | |
|---|---|---|---|
| 2,364,008 | 11/1944 | Stuart | 530/360 |
| 2,489,880 | 11/1949 | Hand et al. | 435/68.1 |
| 2,585,225 | 2/1952 | Carlson | 530/365 |
| 3,698,912 | 10/1972 | Winitz | 530/378 |
| 4,100,024 | 7/1978 | Adler-Nissen | 435/836 |
| 4,293,571 | 10/1981 | Olofsson et al. | 426/656 |
| 4,427,658 | 1/1984 | Maubois et al. | 514/2 |
| 4,452,888 | 6/1984 | Yamazaki et al. | 435/68.1 |
| 4,495,176 | 1/1985 | Brule et al. | 530/360 |
| 4,636,388 | 1/1987 | Lin et al. | 435/68.1 |
| 4,670,268 | 6/1987 | Mahmoud | 426/72 |
| 4,697,004 | 9/1987 | Puski et al. | 530/378 |
| 5,013,653 | 5/1991 | Huston et al. | 435/71.1 |
| 5,039,532 | 8/1991 | Jost et al. | 426/41 |
| 5,112,812 | 5/1992 | Samuelsson et al. | 530/833 |

FOREIGN PATENT DOCUMENTS

| | | |
|---|---|---|
| 022019 | 1/1981 | European Pat. Off. . |
| 65663 | 12/1982 | European Pat. Off. . |
| 087247 | 8/1983 | European Pat. Off. . |
| 226221 | 6/1987 | European Pat. Off. . |
| 250501 | 1/1988 | European Pat. Off. . |
| 274946 | 7/1988 | European Pat. Off. . |
| 302807 | 2/1989 | European Pat. Off. . |
| 322589 | 7/1989 | European Pat. Off. . |
| 2133985 | 12/1972 | France . |
| 2021921 | 12/1979 | United Kingdom . |

OTHER PUBLICATIONS

Perlmann et al, Methods In Enzymology XIX, published 1970 by Academic Press (NY), pp. 113, 132, 133.
Fersht, Enzyme Structure and Mechanism, 2nd Ed., W.H. Freeman and Company, New York, pp. 17–18 (1985).
Mullally, M. et al. J. Agric. Food Chem., 42, 2973–2981, 1994.
Corolase® PP Technische Information und Spezifikation, El–1–07–D, 2 pp, Röhm GmbH, Darmstadt, Germany (Oct. 19, 1995).
The Merck Index, 11th Ed., p. 1109, Merck & Co., Inc. (1989).
Jakobsson I, et al., J. Pediatr. Gastroenter. and Nutri., 2(4), 613–616, 1983.
Asselin J. et al., J. Food Sci., 54(4), 1037–1039, 1989.
Westrom, B.J. et al., Pancreas, 2, 589–596 (1987).
Ohlsson, B. et al., Inter. J. Biochem., 19(7), 633–639 (1987).
Dixon, M. et al., Enzymes 3rd ed., pp. 300–302, and 886, Academic Press, 1979.
Wiseman, A., ed. "Handbook of Enzyme Biotechnology", 6–7, Halsted Press (1975).

*Primary Examiner*—Jeffrey E. Russel
*Attorney, Agent, or Firm*—Gabriel Lopez

[57] ABSTRACT

A whey protein hydrolysate is described which is free of allergenics while preserving the structures susceptible of exerting anticipatory regulations to maximize the tolerance and protein metabolism, and mixtures thereof with casein and/or soy protein hydrolysates. Whey protein hydrolysates according to the invention have an amino acid composition comprising at least 2% by weight of tryptophan, less than 5% by weight of threonine, less than 2.8% by weight of methionine whereby 40 to 60% by weight of the amino acids are in the form of tetra- to decapeptides.

19 Claims, No Drawings

WHEY PROTEIN HYDROLYSATES AND MIXTURES THEREOF WITH CASEIN AND/OR SOY PROTEIN HYDROLYSATES

This is a continuation of application Ser. No. 08/353,652 filed Dec. 9, 1994, now abandoned, which in turn is a continuation of application Ser. No. 07/960,143, filed Oct. 13, 1992, now abandoned, which in turn is a continuation of application Ser. No. 07/591,593, filed Oct. 2, 1990, now abandoned.

The invention provides a controlled protein hydrolysate from cow milk proteins and soy proteins, a process for preparing such hydrolysate and compositions comprising such hydrolysate.

Protein hydrolysates may be used in food for dietary or therapeutic purposes. It is generally accepted that the size of peptides should be small and that the content of free amino acids should be low, to secure optimum absorption by the enteral tract.

Various protein hydrolysates and processes for their manufacture have been suggested. They all show certain drawbacks, with respect to their composition, their manufacture, or both.

The present invention provides an outbalanced and controlled mixture of physiological small peptides which secures optimal absorption and which is moreover free of allergenics and preserves the structures susceptible of exerting anticipatory regulations to maximize the tolerance and protein metabolism and the structure of other biologically active natural peptides.

Such mixture can be obtained employing selected starting materials, enzymes and reaction steps.

The present invention provides a protein hydrolysate of whey protein substantially free of proteins having a molecular weight of more than 60,000.

The whey protein fraction substantially free of proteins having a molecular weight of more than 60,000 is hereinafter designated selected whey protein.

A preferred selected whey protein hydrolysate of the invention is obtained by physiological hydrolysis, involving a gastric phase, i.e. a HCl/pepsin prehydrolysis, followed by an enzymatic treatment of the prehydrolysate with a mixture of trypsin-chymotrypsin with a cationic serine endoprotease type elastase 2.

The introduction of a gastric phase and the use of cationic serine endoprotease type elastase 2, preferably such hydrolyzing at P1 methionine and P1 leucine residues in the whey protein hydrolysis procedure, allow the denaturation of globular proteins such as albumine or globulines and of tertiary and quaternary structures. Such denaturation does not only allow the elimination of allergenic properties but also facilitates the access by the pancreatic enzymes trypsin-chymotrypsin to hydrolysis sites, while preserving the physiological peptide sequences susceptible to induce the reactions of anticipatory regulations and other regulatory functions.

The term cationic serine endoprotease type elastase 2 as used herein relates to enzymes capable of hydrolyzing under alkaline conditions the peptide bonds formed between leucine, phenylalanine, methionine and tyrosine with glycine and alanine and include for example porcine elastase type 2, human pancreatic elastase type 2, and cationic serine endopeptidases having a similar activity.

The whey protein used as starting material for the preparation of the whey protein hydrolysate may be obtained by removal of the proteins and macropeptides present in the protein whey fraction in a manner known per se in the art, e.g. employing anion-exchange resins, but preferably by micro- or ultrafiltration, employing conventional membranes having the required dynamic cut-off capacity.

The whey protein fraction employed will conveniently be substantially free of macrolipids to facilitate enzymatic hydrolysis. (The term macrolipids as used herein refers to the residual milk fat material finely emulsionated in the form of microglobules of triglycerides and polar lipids of the phospholipid and lipoprotein type.) Such macrolipids may be removed prior to the removal of the proteins and macropeptides or simultaneously, e.g. by micro- and/or ultrafiltration. In general it will be preferred to prepare the selected whey protein fraction employed starting from whey protein comprising macrolipids and to subject this material to an ultra- or diafiltration. This procedure has the advantage that it employs membranes having a cut-off capacity of more than 500,000, e.g. of 1,000,000 while resulting in an effective or dynamic cut-off of 50,000 to 100,000.

Depending on the desired qualities of the whey protein fraction employed, the ultrafiltration will be carried out with membranes having a dynamic cut-off capacity in the range of from about 50,000 to about 1000,000, preferably of about 50,000. The term dynamic cut-off capacity as used herein is defined as the cut-off observed after a time of stabilization of the dynamic membrane when ultrafiltrating whey protein solution.

The selected whey protein used as starting material may be delactosed (or not), depending on the contemplated use of the hydrolysate. It is preferably delactosed.

A preferred hydrolysis process of the selected whey protein involves typically the steps of a) heating a solution of selected whey protein in water to 43°±4° C., and subjecting said solution to a pepsin prehydrolysis at pH between 2.0 and 3.0, b) adjusting the pH of the mixture of step a) at a temperature in the range of from 35° to 50° C. to a pH between 7.0 and 9.0 and submitting said mixture to an enzymatic trypsin-chymotrypsin hydrolysis in the presence of a cationic serine endoprotease of type elastase 2, c) pasteurizing the mixture of step b), subjecting it to an ultrafiltration and concentrating and drying the permeate.

The pepsin prehydrolysis according to step a) is conveniently effected with an extract of bovine pepsin, obtainable by extraction of the rennet-stomach of adult cows. The pepsin extract preferably comprises at least 1700 mg pepsin per litre. The ratio of the mass of active chymosin: mass of active bovine pepsin is preferably equal to or smaller than 0.154. The weight ratio pepsin: substrate is conveniently in the range of 1:7500 to 1:2500, preferably about 1:5000. The prehydrolysis is preferably carried out with agitation, more preferably with rhythmic controlled agitation simulating the peristalsis of the stomach.

Where desired, the prehydrolysate is demineralized before subjecting it to the enzymatic hydrolysis of step b). The demineralization may be effected in a manner known per se for the reduction of the chloride, sodium and potassium content, e.g. by ultrafiltration employing membranes allowing to retain a maximum of peptides. Suitable membranes have a cut-off of from 1500 to 15000 e.g. of ca. 10,000. The pH of the prehydrolysate is conveniently adjusted to pH 8±0.1 in a manner known per se. A suitable ultrafiltration temperature is between 30° to 60° e.g. ca. 50° C.; a suitable inlet pressure is conveniently between 2 and 4 bars.

The optionally demineralized mixture of step a) may be rendered alkaline in a manner known per se, e.g. employing electrodialysis, ion exchange resins, ultrafiltration, in organic bases, such as NaOH, KOH, NH$_3$ or mixtures thereof. The bases are preferably added in the form of an aqueous solution. The amount of trypsin-chymotrypsin to be employed will conveniently be selected in the range of from 0.15 to 0.2% by weight (expressed in g enzymes per 100 g substrate; hereinafter expressed as E/S). Preferably the trypsin-chymotrypsin is employed in the physiological ratio. The amount of cationic serine endoprotease type elastase 2 to be employed will conveniently lie in the range of 1 to 5 units per gram protein to be hydrolzsed (whereby 1 unit is the amount of enzyme that will hydrolyze 1.0 μmol of N-Ac-tri-Ala methylester per minute at 25° C., pH 8.5, while hydrolyzing 1.0 μmol of glutaryl-Ala-Ala-Pro-Leu-p-nitroanilide |sequence ID No. 1| and of succinyl-Ala-Ala-Pro-Meth-p-nitro-anilide |sequence ID No. 2|.

The hydrolysis is preferably effected with agitation. Trypsin/chymotrypsin proteolytic enzymatic mixtures (PEM) suitable for use in the invention are commercially available. The enzymatic activity of the trypsin is conveniently in the order of 1800 u. USP/mg or higher, that of chymotrypsin in the order of 350 u. USP/mg or higher (whereby u.USP refers to units according to analytical methods disclosed by United States Pharmacopeia).

The pasteurization of the mixture of step b) is intended to inactivate the enzymes. It is preferably carried out by heating for a very short time, e.g. for less than 2 minutes, more preferably for about 1 minute, at a temperature of slightly less below 100° C., e.g. 98° C. Pasteurization under these conditions will prevent bacterial development if there was any during hydrolysis.

The ultrafiltration will typically be effected in a manner known per se employing membranes having a cut-off capacity in the range of from about 1500 to about 15000, preferably of about 1500 to 10000. The inlet pressure will conveniently be in the range of from 1.5 to 5, e.g. 2 to 3 bars. A suitable temperature is in the range of from 300 to 600, preferably about 50° C. The filterable elements from the retentate are preferably reduced by diafiltration, involving the addition of water and simultaneous or subsequent elimination of an equivalent amount of permeate. The diafiltration is suitably started when the content of dry material in the retentate has reached a certain level, e.g. of 100 g dry material per litre or more. The diafiltration ratio employed is conveniently in the range of 1.0 to 2.5, e.g. 1.5.

The permeate may then be concentrated, e.g. by evaporation, employing for example a falling film evaporator, pasteurized to sterilize the concentrate, e.g. by heating at 950° to 125° and dried in a manner known per se, e.g. by spray-drying.

Before the selected whey protein is subjected to a pepsin prehydrolysis, it is conveniently pasteurized, e.g. by heat treatment at pH 4.6±0.1 at 90° to 92° C. for 60 seconds. The adjustment of the aqueous protein solution to pH 4.6±0.1 is suitably effected with a mineral or organic acid or a mixture thereof, e.g. with HCl or phosphoric acid, conveniently in diluted form.

The pasteurization may also be effected for a longer period of time and/or at temperatures above 90° and below 100° C. According to a preferred embodiment of the invention, the mixture will be heated for 5 up to 10 minutes to change the texture of the selected whey protein before subjecting it to the pepsin prehydrolysis.

The duration of the gastric and pancreatic (chymotrypsin-trypsin-elastase 2) treatment in the hydrolysis steps a) and b) is conveniently selected such that the hydrolysate is in a molecular form which is substantially free of allergenics, whilst preserving the structures susceptible of exerting anticipatory regulations in order to maximize the tolerance, the absorption and the protein metabolism.

The optimum condition may be determined by pilot tests. When the selected whey protein is for example pasteurized at pH 4.6 at 90° for 60 seconds, prior to submission to the optimum condition of steps a) to c), a suitable product may be obtained when the pepsin hydrolysis is effected during 1 hour and the chymotrypsin-trypsin-elastase 2 hydrolysis during 2½ hours.

The selected whey protein hydrolysate of the invention is novel and useful.

Typically, the selected whey protein hydrolysate of the invention comprises from 40 to 60% by weight of its amino acids in the form of oligopeptides having from 4 to 10 amino acids.

It typically comprises per 100 g amino acids (in free form or peptide form or peptide form) at least 2.0 g, typically from 2.2 to 3.0 g tryptophan, not more than 2.8 g, typically from 2.8 to 2.4 g methionine and less than 5 g, more preferably not more than 4.8 g of threonine.

The selected whey protein hydrolysate of the invention will conveniently be employed in nutritionally acceptable composition form. Such composition may contain 1 or more additional protein hydrolysates from different origin (e.g. from rennet casein, from soy protein) and type (e.g. subjected only to a gastric hydrolysis, or solely to a chymotrypsin-trypsin hydrolysis, or solely to a cationic serine endoprotease type elastase 2 hydrolysis or to combinations thereof).

The invention therefore also provides protein hydrolysate mixtures substantially free of allergenic proteins comprising selected whey protein hydrolysate of the invention with a soy protein hydrolysate and/ or with a hydrolysate of casein of which the glycoprotein fraction has been eliminated before subjecting it to hydrolysis.

For the preparation of mixtures of selected whey protein hydrolysate and soy protein hydrolysate, the soy protein used as starting material is preferably cleared of phytate and phenolic compounds.

The soy protein may be hydrolyzed analogous to steps a) to c) described for the process of the preparation of the selected whey protein hydrolysate. If so desired, the soy protein may be admixed with the selected whey protein and optionally pasteurized before subjecting the mixture to a pepsin prehydrolysis according to step a).

Particularly useful protein hydrolysates are for example obtained when employing the starting materials soy proteins and selected whey proteins in a weight ratio of about 1:1 based on the protein content of said fraction. The whey/soy protein mixture is preferably pasteurized e.g. by heating at about 90° to 92° C. for a short time, for example ca. 60 seconds, at a pH of 4.6±0.1. The adjustment of the aqueous protein solution to pH 4.6±0.1 is suitably effected with an inorganic or organic acid such as HCl, lactic acid etc.

Said pasteurized mixture may then be subjected to process steps a) to c) described hereinabove.

Depending on the intended use of the protein hydrolysate of the invention and on commercial considerations, the soy protein starting material may for example be subjected only to a chymotrypsin-trypsin hydrolysis or only to a chymotrypsin-trypsin hydrolysis in the presence of a cationic serine endopeptidase type elastase 2. In the latter case, a solution of soy protein in water may for example be added to the selected whey protein prehydrolyzed according to step a).

This mixture is conveniently pasteurized before subjecting it to further hydrolysis, for example according to step b).

The without glycoprotein fraction employed as a starting material for the preparation of protein hydrolysate mixtures with a selected whey protein hydrolysate may be obtained in a manner known per se in the art. e.g. by enzymatic precipitation of the protein fraction from milk. Such enzymatic precipitation is conveniently effected with rennet.

Depending on the particular needs, the casein without glycoprotein fraction may be hydrolyzed analogous to the procedure of steps a) to c) described hereinabove and then admixed with the selected whey protein hydrolysate and optionally soy protein hydrolysate, or the selected whey protein hydrolysate and optionally soy protein hydrolysate may for example be admixed with a hydrolysate of casein without glycoprotein fraction that was not subjected to a gastric prehydrolysis, or solely subjected to a gastric prehydrolysis, or subjected only to a gastric prehydrolysis and a cationic serine endoprotease type elastase 2 hydrolysis.

A particularly preferred product of the invention is the protein hydrolysate mixture of selected whey protein hydrolysate, soy protein hydrolysate and hydrolysate of casein without glycoprotein fraction of which each component was subjected to process steps a) to c).

The selected whey protein employed as starting material will then conveniently be delactosed.

The weight ratio of the starting materials soy protein, selected whey protein and casein without glycoprotein fraction may vary within certain ranges. Preferably, the weight ratio of the starting materials of said soy/whey/casein protein hydrolysate is selected such that the lysine: arginine ratio of the final product (hereinafter soy/whey/casein protein hydrolysate mixture of the invention) is below 2, more preferably below 1.75, e.g. between 1.35 to 1.75, particularly below 1.6, most preferably between 1.35 and 1.6. Particularly preferred products according to the invention are obtained when employing the starting materials soy proteins, selected whey protein and casein without glycoprotein fraction, in a weight ratio of about 1:1:1 (hereinafter the 1:1:1 protein hydrolysate of the invention).

The 1:1:1 protein hydrolysate of the invention has a very low H+ ion load, due to its reduced content of organic phosphorous compounds, in particular of phosphoproteins and of sulfur containing amino acids. The 1:1:1 protein hydrolysate of the invention has a lysine/arginine ratio which is very near to that present in mother milk (1.44). Such ratio is susceptible to favorably influence the insulin/glucagon balance. The high arginine content of the hydrolysate of the invention is favorable in situations of enteral reanimation and wound cicacitration. Due to its outbalanced composition of physiological small peptides derived from a mixture of animal and vegetable proteins, it facilitates the hydrolysis of the small peptides and subsequent adsorption and is indicated for use in therapeutic nutrition in situations of stress, of high catabolism, of cicatrisations and results in a very low Blood Urea Nitrogen (BUN) and, consequently, a very low Renal Solute Load.

The amino acids (in free form or peptide form) of the whey/soy/casein protein hydrolysate of the invention comprise conveniently less than 3.5% by weight, preferably less than 3% by weight, more preferably from 2.5 to 2.7% by weight of sulfur-containing amino acids (whereby the content in % by weight relates to the total content of sulfur containing amino acids in free form and peptide form).

The hydrolysis conditions are selected such that 70 to 90% by weight of the amino acids of the hydrolysate are in the form of di-to octapeptides and less than 15% by weight preferably less than 10% by weight are in free (amino acid) form.

Another preferred embodiment of the invention is a protein hydrolysate mixture of selected whey protein hydrolysate with an hydrolysate of casein without glycoprotein fraction, in which the selected whey protein and preferably also the casein component have been subjected to process steps a) to c), which mixture is substantially free from allergenic proteins.

The weight ratio of the selected whey protein hydrolysate and the hydrolysate of casein without glycoprotein fraction may vary between certain ranges.

Particularly preferred mixtures are obtained when employing the starting materials selected whey protein and casein without glyco-protein fraction in a weight ratio in the range of from 5:1 to 1:1 and subjecting each component to the process steps a) to c) (herein-after whey/casein protein hydrolysate of the invention). The selected whey protein is conveniently pasteurized according to the conditions described above, prior to subjecting it to process step a).

Such protein hydrolysate mixtures take into account the particularities of infants (such as, depending on their development phase, weak HCl secretion, limitation of gastric proteolysis, absence of elastases, particularly of elastase type 2, their limited ability to digest proteins present in mother milk such as immunoglobulins and other biologically important proteins, while preserving the protective and regulatory activity of said proteins) and provides a hydrolysate from which allergenics have either been eliminated (immunoglobulins $G_1$, $G_2$, A, M, secretory component, casein macropeptides) or destroyed ($\beta$-lacto-globulins and other proteins or macropeptides by a physiological hydrolysis involving a gastric (chlorhydro-peptic) and elastase type 2 phase).

At least 45% by weight, more preferably at least 60% by weight, particularly 70 to 90% by weight of the amino acids of the whey/casein protein hydrolysate of the invention are in the form of di- to octapeptides and less than 20% by weight, more preferably less than 15% by weight, particularly less than 10% by weight of amino acids of the whey/casein protein hydrolysate of the invention are in free (amino acid) form.

The use of selected whey protein in the whey/casein protein hydrolysate of the invention results in a reduction of the threonine content, a lower though sufficient valine content and an increased tryptophan content. According to a further preferred embodiment of the invention, the amino acids of the whey/casein protein hydrolysate of the invention comprise 4.8% by weight or less threonine. Thus, the amino acids of the whey/casein protein hydrolysate of the invention from selected whey protein: casein in a weight ratio 4:1 and 1:1 will have a threonine content in the range of from 3.9% to 4.8% by weight, e.g. from 4.55 to 4.8% by weight, (whereby the content in % by weight relates to the total threonine content, i.e. in peptide or free amino acid form). Such hydrolysate is indicated for administration to infants. For administration to adults, it will, in general, be indicated to increase such threonine content.

The protein hydrolysates according to the invention are conveniently administered in nutritionally acceptable composition form. Such compositions form also part of the invention and may comprise carbohydrate and fatty acid sources, vitamins, minerals and trace elements.

According to a preferred embodiment of the invention, the compositions of the invention are in the form of a complete formula diet (in liquid or powder form), such that, when used as sole nutrition source essentially all daily caloric, nitrogen, fatty acid, vitamin, mineral and trace element requirements are met.

For infants, the daily caloric amount to be supplied will in general lie in the range of from 100 to 180 Kcal per kg body weight. The contribution of the nitrogen source (i.e. the whey/casein hydrolysate of the invention), carbohydrate source and lipid source to the total daily amount may vary within wide ranges. In typical compositions of the invention the carbohydrate source provides for 45 to 68% , the fatty acid sources for 25 to 50% and the protein hydrolysate of the invention for 7 to 15% of the total energy supply of the composition.

An example of carbohydrates particularly suitable for use in the complete diet for infants includes a mixture on the basis of maltodextrines (10 to 25%) and lactose (90 to 75%), unless the infant requires a diet having a low lactose content, in which case the carbohydrate source will conveniently be quasi exempt of lactose (<1% lactose).

Prefer red compositions comprising a whey/soy/casein protein hydrolysate according to the invention are for enteral use, e.g. for oral administration and/or tube feeding (e.g. nasal gastric or nasal jejunum or gastro-stomach feeding). Such compositions are conveniently administered in the form of an aqueous liquid. The compositions suitable for enteral application are accordingly preferably in aqueous form or in powder form, whereby the powder is conveniently added to water prior to use. For use as tube feeding, the amount of water to be added will depend on the patient's fluid requirement and condition.

The compositions of the invention may be employed as food supplement, as complete diet or for therapeutic nutrition.

For adults, the daily caloric amount to be supplied will, in general, lie in the range of from 750 to 3500 Kcal. The contribution of the nitrogen source (i.e. the hydrolysate of the invention), carbohydrate source and lipid source to the total daily amount may vary within wide ranges. In typical compositions of the invention the carbohydrate source provides for 30 to 88% , the fatty acid sources for 5 to 45% and the protein hydrolysate of the invention for 7 to 25% of the total energy supply of the composition.

Examples of suitable fatty acid sources include triglyceride oils and phospholipids. p referred triglyceride oils are rich in short and/or medium chain fatty acid residues (i.e. residues of $C_4$ to $C_{12}$ fatty acids) and comprise preferably also unsaturated fatty acid residues. Such fatty acid residues may be mono-, poly- (from C18 PUFA) or highly unsaturated (from C20 and C22 HUFA), whereby PUFA stands for polyunsaturated fatty acids and HUFA for highly unsaturated fatty acids. Preferably the triglyceride source provides a balance between the various types of unsaturated fatty acids, in particular between monounsaturated omega-9, polyunsaturated omega-6 and omega-3 and highly unsaturated omega-6 and omega-3, fatty acids.

The PUFA or HUFA of the omega-6 and omega-3 type may be added in a manner known in the art, taking into account the balance vis-a-vis oleic acid. The unsaturated fatty acids (in free form or triglyceride form) will conveniently be added such that the ratio oleic acid: linoleic acid: alphalinolenic acid will be in the range of 10 to 24:6:1 (6 including the totality of omega 6 fatty acids and 1 including the totality of omega 3 fatty acids).

The carbohydrates employed for composition for adults are preferably primarily a mixture on the basis of maltodextrines having a low mono- and disaccharide content (<5% by weight of the total carbohydrate content), a very low content of alimentary fibres and being quasi exempt of lactose. Preferably such compositions will have a total lactose content of less than 1% by weight of the protein hydrolysate present in the formulation.

Examples of vitamins suitable for incorporation in the composition of the invention include vitamin A, vitamin D, vitamin E, vitamin K, vitamin C, folic acid, thiamin, riboflavin, vitamin $B_6$, vitamin $B_{12}$, niacin, biotin, carnitine, choline and panthotenic acid in physiologically acceptable form. Depending on the contemplated use, the incorporation of taurine and/or hypotaurine, resp. supplementation of threonine, may be useful.

Examples of minerals and trace elements suitable for incorporation in the composition of the invention include sodium, potassium, calcium, phosphorus, magnesium, manganese, copper, zinc, iron, selenium, chromium and molybdenum in physiologically acceptable form.

It will be appreciated that the minimum daily requirements of vitamins, minerals and trace elements will depend on the person to be treated. In general, the daily minimum requirements are determined by governmental authorities; they may accordingly vary from country to country.

Where oral application is intended, the composition comprises preferably also flavoring agents.

An aqueous liquid composition suitable for tube feeding will conveniently have an osmolality in the range of from 270 to 400 mOsm/kg $H_2O$. If the product is intended for use as a complete diet, its concentration may be higher when the product is diluted prior to use.

In the following examples, which illustrate the invention, % and parts are by weight unless stated otherwise and temperatures in centigrades.

EXAMPLE 1

Pasteurization of a Soya/Selected Whey Protein Mixture

In a vessel of 12 $m^3$ are introduced 5.3 $m^3$ of water at room temperature.

Thereto are added, portionwise, 200 kg of commercially available soya protein powder (having a protein content of 91.5% by weight of dry material and cleared of phytate and phenol compounds by an ion exchange procedure) and 200 kg of selected whey protein powder (according to Example 2 hereinafter). The mixture is stirred till hydration is completed (after ca. 2 hours), then adjusted at pH 4.6±0.1 with diluted hydrochloric acid (ca. 1N) and then subjected to a flash heat treatment at 90° C. for 60 seconds.

EXAMPLE 2

Preparation of Selected Whey Protein

Commercially available delactosed lactoserum protein powder is pretreated to remove macrolipids and large protein having a molecular weight of more than 60.000 such as immunoglobulins, bovine serum albumin and enzymes. This treatment is carried out by microfiltration and/or ultrafiltration on membrane having a dynamic cut-off over 50,000.

The elimination of large proteins may also be effected with chromatographic techniques such as ion exchange chromatography.

In a whey protein, purified by ultrafiltration, 95% of the immunoglobulins IgG are eliminated by microfiltration on membrane 0.22 micron, measured by immunotechnic.

Where delactosed whey protein is employed a product is obtained having a composition comprising min. 80% of proteins and less than 2% of lactose.

Where desired the permeate may then be subjected to pasteurization, e.g. at 95° C. during 10 minutes, or by a flash heat treatment as described in Example 1.

EXAMPLE 3

Pepsin Hydrolysis of the Soya/Selected Whey Protein Mixture

The mixture according to Example 1 is placed in a 12 m³ vessel and its temperature adjusted to 43°±4° C. The mixture is acidified with diluted hydrochloric acid (1N) up to a pH of 2.5±0.1. Then are added 38.8 l of bovine pepsin extract (we employed BOVIPEP, a bovine pepsin extract commercially available from Lab. Présure-Granday having a min. pepsin content of 1.7 g/l, and the reaction vessel shuttled for 1 hour.

EXAMPLE 4

Soya/Selected Whey Protein Hydrolysate a) The temperature of the mixture according to Example 3 is adjusted to 45°±2° C. The mixture is then adjusted to pH 8±0.1 employing an aqueous alkaline solution comprising in 150 l 12 kg of NaOH, 18.65 kg of KOH, 43 l of 21% ammonia solution and water;

b) 1 m³ of the thus obtained mixture is placed in a reaction vessel of 12 m³. Thereto are added 647 g of a mixture of proteolytic enzymes, containing the pancreatic enzymes trypsin and chymotrypsin in purified form and 277 g of an elastase type 2 preparation. We employed PEM 2500S, a trypsin/chymotrypsin mixture commercially available from NOVO INDUSTRIE ENZYMES S.A. (Paris) having a trypsin activity of at least 1800 u. USP/mg and a chymotrypsin activity of at least 350 u. USP. The elastase preparation employed was a water-soluble powder obtained from porcine pancreas type 2 elastase having an enzymatic activity of 30 I.U./mg (activity on N-Ac-tri-ala methylester).

After complete dissolution of the enzymes the remaining part of the mixture according to Example 4a is added at a rate of 17 m³ per hour. This takes approximately 15 minutes. The reaction vessel is then shuttled for two and a half hours while maintaining the temperature at 45°±2° C. The pH is regularly controlled and adjusted at 8±0.2 employing the neutralization solution used in step 4a).

EXAMPLE 5

Soya/Selected Whey Protein Hydrolysate Concentrate a) The mixture according to Example 4b) is pasteurized by a flash heat treatment at 98° C. for 60 seconds.

b) The pasteurized reaction mixture is then subject to an ultrafiltration employing SFEC membranes having a cut-off of 10000 and a membrane surface of 170 m² (but an inferior dynamic cut-off). The inlet pressure is between 2 and 3 bars, the temperature 50° C.

The ultrafiltration is followed by a diafiltration when the retentate attains a dry matter content of 130 g/l. The diafiltration degree employed is 1.5. The adaption of the mineral content to the desired purpose is realized by electrodialysis or with ion exchangers.

The permeate is then cooled, stored in a vessel of 60 m³, concentrated up to a concentration of about 350 g protein hydrolysate per litre pasteurized at 95° C., and the concentrate spray dried with air at an inlet temperature of 180° C. The thus obtained product has the following physiochemical characteristics:

| | |
|---|---|
| Dry extract | 94.39 ± 0.36 g/100 g |
| Ashes | 8.94 ± 0.10 g/100 g |
| Total Nitrogen content (Kjeldahl) | 13.27 ± 0.01 g/100 g |
| Content of N in the form of free amino groups[1] | <3 g/100 g total N |
| Total content of N in NH or $NH_2$ form | 10.73 g/100 g |
| Proteins[2] content | 85.46 ± 0.06 g/100 g |
| Lipids | 0.17 g/100 g |
| Glucides | 3.11 g/100 g |
| Lactose | 1.10 g/100 g |
| Solubility | 99.8% |
| pH | 5.87 |
| Composition in Amino Acids (in g/100 g) | |
| Lysine | 6.36 |
| Histidine | 1.80 |
| Arginine | 4.54 |
| Aspartic acid | 9.33 |
| Threonine | 3.96 |
| Serine | 4.31 |
| Glutamine | 15.88 |
| Proline | 4.59 |
| Glycine | 2.40 |
| Alanine | 3.74 |
| Cystine | 1.38 |
| Valine | 4.13 |
| Methionine | 1.14 |
| Isoleucine | 4.04 |
| Leucine | 7.46 |
| Tyrosine | 2.79 |
| Phenylalanine | 3.38 |
| Tryptophan | 1.38 |
| Distribution of molecular weight in % | |
| MW > 5000 | 0 |
| 1400 < MW < 5000 | 26.40 |
| MW < 1400 | 73.40 |

Total content of free amino acids:
<4.6 g/100 g powder
Degree of Hydrolysis $$\text{Effective:} \frac{g \text{ of N in free NH}_2 \text{ groups}}{g \text{ of total N(NH, NH}_2\text{)}} \times 100 = 27.95\%$$

$$\text{Apparent:} \frac{g \text{ of N in free NH}_2 \text{ groups}}{g \text{ of total N (Kjeldahl)}} \times 100 = 22.60\%$$

[1] by standard method, employing 2,4,6-trinitrobenzene sulfonic acid as reactant and detection at 420 nm.
[2] calculated by multiplying the total nitrogen content determined according to Kjeldahl with the factor 6.44.

EXAMPLE 6

Pepsin Prehydrolysis of Rnnet Casein a) 400 kg of rennet casein (obtained from casein by mild enzymatic precipitation with rennet, comprising at least 84% by weight of proteins-relative to the total dry material and having a water content of 10% or less) are added portionwise with stirring to a reaction vessel of 12 m³ comprising 3.3 m³ of water, cooled at a temperature of 5° C., the rennet casein is dissolved after about 2 hours.

b) The pH of the solution of step 6a) is adjusted to 2.5±0.1 employing a phosphoric acid solution. The acidified reaction mixture is heated to 43°±2° C. and then treated with 38.6 l bovine pepsin extract (analogous to the procedure of Example 3).

EXAMPLE 7

Trypsin/Chymotrypsin/Elastase Type 2 Hydrolysis of Prehydrolyzed Rennet Casein a) The temperature of the mixture according to Example 6 is adjusted to 45°±2° C. The mixture is then adjusted to pH 8±0.1 employing the aqueous alkaline solution defined in Example 4a).

b) 660 litres of the thus obtained mixture are placed in a reaction vessel. Thereto are added 643 g of the trypsin/chymotrypsin mixture and 275 g of the elastase preparation defined in Example 4b). After complete dissolution of the enzymes, the remaining part of the mixture according to step 7a) is added at a rate of 10.5 m³/hour. This takes about 15 minutes.

The reaction vessel is then shuttled for two and a half hours while maintaining the temperature at 45°±2° C. The pH is regularly controlled and adjusted at 8±0.2 employing the neutralization solution used step 7a).

EXAMPLE 8

Pasteurization of the Rennet Casein Hydrolysate a) The mixture according to Example 7b) is pasteurized by a flash heat treatment at 98° C. for 60 seconds.

b) The pasteurized reaction mixture is subject to ultrafiltration, diafiltration and then cooled and concentrated analogous to the procedure of Example 5b), pasteurized at 98° C. for 60 seconds and then dried with hot air (180° C).

The thus obtained product has the following physiochemical characteristics:

| | | |
|---|---|---|
| Dry extract | 93.18 ±0.28 | g/100 g |
| Ashes | 15.51 | g/100 g |
| Total N content (Kjeldahl) | 13.23 ±0.37 | g/100 g |
| Content of N in the form of free NH₂ groups | 2.42 ±0.36 | g/100 g total N |
| Total content of N in NH or NH₂ form | 11 | g/100 g |
| Protein content (Kjeldahl × 6.38) | 84.40 | g/100 g |
| Lipids | 0.36 | g/100 g |
| Glucides | 0.40 | g/100 g |
| Lactose | 0.46 | g/100 g |
| Solubility | 98% | |
| pH | 6.39 | |
| Composition in Amino Acids (in g/100 g) | | |
| Lysine | 5.92 | |
| Histidine | 2.23 | |
| Arginine | 2.82 | |
| Aspartic acid | 5.50 | |
| Threonine | 2.88 | |
| Serine | 4.06 | |
| Glutamic acid | 16.80 | |
| Proline | 7.79 | |
| Glycine | 1.36 | |
| Alanine | 2.07 | |
| Cystine | 0.37 | |
| Valine | 4.89 | |
| Methionine | 1.83 | |
| Isoleucine | 3.59 | |
| Leucine | 7.23 | |
| Tyrosine | 4.37 | |
| Phenylalanine | 3.91 | |
| Tryptophan | 1.13 | |
| Distribution in molecular weight in % | | |
| MW > 5000 | 0 | |
| 1400 < MW < 5000 | 62.50 | |
| MW < 1400 | 37.40 | |
| Total content of free amino acids | | |
| 0.65 g / 100 g powder | | |
| Effective degree of hydrolysis | 22% | |
| Apparent degree of hydrolysis | 18.3% | |

EXAMPLE 9

Pasteurization of Aqueous Solution of Selected Whey Protein

In a vessel of 12 m³ are introduced 5.3 m³ of water at room temperature.

Thereto are added, portionwise, 400 kg of selected whey protein powder (according to Example 2). The mixture is stirred till hydration is completed (after ca. 2 hours), then adjusted at pH 4.6±0.1 with diluted hydrochloric acid (ca. 1N) and then subjected to a flash heat treatment at 80° C. for 60 seconds.

EXAMPLE 10

Pepsin Hydrolysis of the Selected Whey Protein

The product according to Example 9 is placed in a 12 m³ vessel and its temperature adjusted to 43°±4° C. The mixture is acidified with diluted hydrochloric acid (1N) up to a pH of 2.5±0.1. Then are added 35.3 l of bovine pepsin extract (we employed BOVIPEP, a bovine pepsin extract commercially available from Lab. Présure-Granday having a min. pepsin content of 1.7 g/l) and the reaction vessel shuttled for 1 hour.

EXAMPLE 11

Selected Whey Protein Hydrolysate a) The temperature of the prehydrolysate according to Example 10 is adjusted to 45°±2° C. The mixture is then adjusted to pH 8±0.1 employing an aqueous alkaline solution comprising in 150 l 12 kg of NaOH, 18.65 kg of KOH, 43 l of 21% ammonia solution and water;

b) 1 m³ of the thus obtained mixture is placed in a reaction vessel of 12 m³. Thereto are added 588 g of a mixture of proteolytic enzymes, containing the pancreatic enzymes trypsin and chymotrypsin in purified form and 252 g of an elastase preparation. We employed PEM 2500S, a trypsin/chymotrypsin mixture commercially available from NOVO INDUSTRIE ENZYMES S.A. (Paris) having a trypsin activity of at least 1800 u. USP/mg and a chymotrypsin activity of at least 350 u. USP. The elastase preparation employed was a water-soluble powder obtained from porcine pancreas type 2 elastase having an enzymatic activity of 30 units/mg (supplied by BIOZYME, for the definition of "unit" see Example 4).

After complete dissolution of the enzymes the remaining part of the mixture according to Example 11a is added at a rate of 17 m³ per hour. This takes approximately 15 minutes.

The reaction vessel is then shuttled for ca. two hours while maintaining the temperature at 45°±2° C. The pH is regularly controlled and adjusted at 8±0.2 employing the neutralization solution used in step 11a).

EXAMPLE 12

Selected Whey Protein Hydrolysate Concentrate a) The mixture according to Example 11b) is pasteurized by a flash heat treatment at 98° C. for 60 seconds.

b) The pasteurized reaction mixture is then subjected to an ultrafiltration employing SFEC membranes having a cut-off of 10000 and a membrane surface of 170 m² (but an inferior dynamic cut-off). The inlet pressure is between 2 and 3 bars, the temperature 50° C.

The ultrafiltration is followed by a diafiltration when the retentate attains a dry matter content of 130 g/l. The diafiltration degree employed is 1.5.

The permeate is then cooled, stored in a vessel of 60 m³, concentrated up to a concentration of about 350 g protein hydrolysate per litre pasteurized at 95° C., and the concentrate spray dried with air at an inlet temperature of 180° C. The thus obtained product has the following physiochemical characteristics:

| | | |
|---|---|---|
| Dry extract | 93.56 ± 0.61 | g/100 g |
| Total Nitrogen content (Kjeldahl) | 11.82 ± 0.01 | g/100 g |
| Content of N in the form of free amino groups[1] | 2.98 | g/100 g total N |
| Total content of N in NH or NH$_2$ form | 11 | g/100 g |
| Proteins[2] content | 76.83 ± 0.09 | g/100 g |
| Lipids | 0.53 | g/100 g |
| Glucides | 8.09 | g/100 g |
| Lactose | 8.57 | g/100 g |
| Solubility | 99.8% | |
| pH | 5.57 | |
| Composition in Amino Acids (in g/100 g) | | |
| Lysine | 9.63 | |
| Histidine | 1.67 | |
| Arginine | 2.13 | |
| Aspartic acid | 11.93 | |
| Threonine | 4.42 | |
| Serine | 3.93 | |
| Glutamic acid | 16.26 | |
| Proline | 5.65 | |
| Glycine | 1.71 | |
| Alanine | 4.77 | |
| Cystine | 1.95 | |
| Valine | 4.26 | |
| Methionine | 1.96 | |
| Isoleucine | 4.92 | |
| Leucine | 11.41 | |
| Tyrosine | 3.30 | |
| Phenylalanine | 3.45 | |
| Tryptophan | 2.30 | |

[1]by standard method, employing 2,4,6-trinitrobenzene sulfonic acid as reactant and detection at 420 nm.
[2]calculated by multiplying the total nitrogen content determined according to Kjeldahl with the factor 6.5.

| Distribution of molecular weight in % | |
|---|---|
| MW > 5000 | 0 |
| 1400 < MW < 5000 | 26.25 |
| MW < 1400 | 73.30 |
| Total content of free amino acids: | |
| 4.6 g / 100 g powder | |
| Degree of Hydrolysis | |
| Effective: | = 30.70 |
| Apparent: | = 28.60 |

EXAMPLE 13

Pasteurization of Selected Whey Protein

In a vessel of 12 m³ are introduced 2.6 m³ of water at room temperature.

Thereto are added, portionwise, 200 kg of selected delactosed whey protein powder (according to Example 2 hereinbefore). The solution is stirred till hydration is completed, adjusted at pH 4.6±0.1 with diluted mixture of hydrochloric acid, citric acid and lactic acid and then subjected to a flash heat treatment at 92° C. for 60 seconds.

EXAMPLE 14

Pepsin Hydrolysis of Selected Whey Protein

The whey protein solution according to Example 13 is placed in a 12 m³ vessel and its temperature adjusted to 43°±4° C. The mixture is acidified with diluted hydrochloric acid (1N) up to a pH of 2.5±0.1. Then are added 38.8 1 of bovine pepsin extract (we employed BOVIPEP, a bovine pepsin extract commercially available from Lab. Présure-Granday having a min. pepsin content of 1.7 g/l) and the reaction vessel shuttled for 1 hour.

EXAMPLE 15

Pasteurization of the Mixture of Pepsin Hydrolysed Selected Whey Protein and Soy Protein a) The temperature of the mixture according to Example 14 is adjusted to 45°±2° C. The mixture is then adjusted to pH 3.8±0.1 employing an aqueous alkaline solution KOH and ammonia.

b) In a vessel of 5 m³ are introduced 2.6 m³ of demineralized water at the temperature of 45° C.±2°. Thereto are added 200 kg of soy protein as isolate. After complete hydration, the pH is adjusted to pH 7±0.1.

c) The products of Example 15a) and 15b) are mixed and kept under agitation until complete homogeneity.

d) The mixture is heat treated at 92° C. for 60 seconds.

EXAMPLE 16

Soy/Selected Whey Protein a) The temperature of the mixture according to Example 15 is adjusted to 45° C.±2° C. The mixture is then adjusted to pH 8.0±0.1 employing an alkaline solution of ammonia and potassium hydroxide.

b) 1 m³ of the thus obtained mixture is placed in a reaction vessel of 12 m³. Thereto added 682 g of a mixture of proteolytic enzymes, containing the pancreatic enzymes trypsin and chymotrypsin in purified form and 834 ml of an elastase preparation. We employed PEM 2500S, a trypsin/chymotrypsin mixture commercially available from NOVO INDUSTRIE ENZYMES S.A. having a trypsin activity of at least 1800 U. USP/mg and a chymotrypsin activity of at least 350 U. USP/mg. The elastase preparation employed was a liquid form obtained from porcine pancreas type 2 elastase (as defined in Example 4). The solution contained 25 g of protein and the activity was 81 unit per mg of protein.

After complete dissolution of the enzymes the remaining part of the mixture according to Example 16a) is added at a rate of 17 m³ per hour. This takes approximately 15 minutes. The reaction vessel is then shuttled for two and a half hours while maintaining the temperature at 45°±2° C. The pH is regularly controlled and adjusted at 8±2 employing the same alkaline solution used previously.

EXAMPLE 17

Soya/Selected Whey Protein Hydrolysate Concentrate a) The mixture according to Example 16b) is pasteurized by a flash heat treatment at 98° C. for 60 seconds.

b) The pasteurized reaction mixture is then subjected to an ultrafiltration employing SFEC membranes having a cutoff of 10000 and a membrane surface of 170 m² (but an inferior dynamic cut-off). The inlet pressure is between 2 and 3 bars, the temperature 500° C.

The ultrafiltration is followed by a diafiltration when the retentate attains a dry matter content of 130 g/l. The diafiltration degree employed is 1.5. The adaption of the mineral content to the desired purpose is realized by electrodialysis or employing ion exchangers.

The permeate is then cooled, stored in a vessel of 60 m³, concentrated up to a concentration of about 350 g protein hydrolysate per litre pasteurized at 95° C., and the concentrate spray dried with air at an inlet temperature of 180° C. The thus obtained product has the following physiochemical characteristics:

| Composition of the product: g/100 g | |
| --- | --- |
| Dry Extract | 96.4 |
| Ashes | 8.8 |
| Total Nitrogen | 13.1 |
| Nitrogen in the form of free amino groups* | 2.7 |
| Protein content** | 84.44 |
| Lipids | none |
| Lactose | 1.0 |
| Solubility | 99.8% |
| pH | 6.4 |
| Composition in amino acids (in g/100 g of amino acids). | |
| Lysine | 8.9 |
| Histidine | 2.3 |
| Arginine | 5.25 |
| Aspartic acid | 11.5 |
| Threonine | 4.4 |
| Serine | 4.6 |
| Glutamic acid | 18.4 |
| Proline | 5.1 |
| Glycine | 2.8 |
| Alanine | 4.5 |
| Cystine | 1.4 |
| Valine | 4.2 |
| Methionine | 1.5 |
| Isoleucine | 4.4 |
| Leucine | 9.6 |
| Tyrosine | 4.0 |
| Phenylalanine | 5.1 |
| Tryptophan | 1.7 |
| Distribution of molecular weight in % | |
| MW > 5000 | 0 |
| 1400 < MW < 5000 | 23 |
| MW < 1400 | 77 |
| Degree of hydrolysis Apparent: | 20% |

*by standard method, employing 2,4,6-trinitrobenzene sulfonic acid as reactant and detection at 420 nm.
**calculated by multiplying the total nitrogen content determined according to Kjeldahl with the K factor of 6.44.

EXAMPLE 18

Trypsin/Chymotrypsin/Elastase-Type 2/Hydrolyse of Rennet Casein a) 400 kg of rennet casein (obtained from milk by enzymic precipitation with rennet, comprising at least 84% by weight of proteins-relative to the total dry material and having a water content of 10% or less) are added portionwise with stirring to a reaction vessel of 12 m³ comprising 3.3 m³ of water, cooled at a temperature of 5° C. The rennet casein is dissolved after 2 hours.

b) The pH of the solution of step a) is adjusted to pH 8±0.1 employing an alkaline solution of ammonia and potassium hydroxide.

c) The temperature is adjusted to 45° C.±2° C.

d) 660 litres of the thus obtained mixture are placed in a reaction vessel. Thereto are added 643 g of the trypsin/chymotrypsin mixture and 786 ml of the elastase solution, defined in Example 16b). After complete dissolution of the enzymes, the remaining part of the protein solution is added at a rate of 10.5 m³ per hour. This takes about 15 minutes.

The reaction vessel is then shuttled for two and a half hours while maintaining the temperature at 42°±2° C. The pH is regularly controlled and adjusted at 8±0.1, employing the neutralization solution used in Example 15a).

EXAMPLE 19

Pasteurization of the Rennet Casein Hydrolysate a) The mixture according to Example 18d) is pasteurized by a flash heat treatment at 98° C. for 60 seconds.

b) The pasteurized reaction mixture is subjected to ultrafiltration, diafiltration and then cooled and concentrated analogous to Example 17b), sterilized at 125° C.±2° C. and then spray dried with air at an inlet temperature 180° C.

The thus obtained product has the following physical characteristics (in g/100 g):

| Dry extract | | | 97.2 |
| --- | --- | --- | --- |
| Total Nitrogen (Kjeldahl) | | | 14.0 |
| Content of N in the form of $NH_2$ groups | | | 2.7 |
| Lipids | | | none |
| Lactose | | | 0.4 |
| Solubility | | | 98.0% |
| pH | | | 7.7 |
| Amino acid composition (g/100 g of Amino Acids) | | | |
| Lys | 8.2 | Gly | 1.7 |
| His | 3.0 | Ala | 2.6 |
| Arg | 3.6 | Cys | 0.4 |
| Asp | 6.3 | Val | 5.5 |
| Thr | 3.4 | Met | 3.0 |
| Ser | 4.0 | Ile | 3.9 |
| Glu | 19.8 | Leu | 9.6 |
| Pro | 11.2 | Tyr | 6.4 |
| | | Phe | 6.0 |
| | | Trp | 1.25 |
| Distribution in molecular weight in % | | | |
| MW > 5700 | | | 0 |
| 1400 < MW < 5700 | | | 20 |
| 300 < MW < 1400 | | | 65 |
| MW < 300 | | | 15 |
| Effective degree of hydrolysis: | | | 20% |

EXAMPLE 20

Demineralized Selected Whey Protein Hydrolysate a) The temperature of the prehydrolysate according to Example 14 is adjusted to 45° C.±2° C. The mixture is then adjusted to pH 8±0.1 employing an aqueous alkaline solution comprising in 150 l, 25.25 kg of KOH, 83.5 l of 21% ammonia solution and water.

b) 3 m³ of the thus obtained mixture, pH reajusted, are ultrafiltered employing Rhône-Poulenc membranes having a cut-off of 10000 and a membrane area of 80 m². The temperature is 50° C. The inlet pressure is between 2 and 4 bars.

The volume is reduced by a factor of about 2.3. The retentate containing the peptides has a chloride content of 1.9 g/l.

c) 1.3 m³ of the thus obtained mixture is placed in a reaction vessel. Thereto are added 341 g of a mixture of proteolytic enzymes, containing the pancreatin enzymes trypsin and chymotrypsin in purified form and 411 ml of an elastase preparation. A suitable trypsin/chymotrypsin mixture is PEM 2500 S, commercially available from NOVO-Industrie Enzymes S.A. (Paris), having a trypsin activity of at least 1800 U. USP/mg and a chymotrypsin activity of at least 350 U. USP/mg.

A suitable elastase preparation is a solution obtained from porcine pancreas type 2 elastase having an enzymatic activity of 1420 Unites/ml (supplied by Biozyme; for the definition of "Unit", see Example 4).

After complete dissolution of the enzymes the remaining part of the mixture according to Example 20a is added at a rate of 17 m³ per hour. The reaction vessel is then shuttled for two and a half hours while maintaining the temperature at 45°±2° C. The pH is regularly controlled and adjusted at 8±0.2 employing the neutralization solution used in step 20a).

EXAMPLE 21

Demineralized Selected Whey Protein Hydrolysate Concentrate a) The mixture according to Example 20c) is pasteurized by a flash heat treatment at 98° C. for 60 seconds.
b) The pasteurized reaction mixture is then subjected to an ultrafiltration employing SFEC membranes having a cut-off of 10000 and a membrane surface of 170 m² (but an inferior dynamic cut-off). The inlet pressure is between 2 and 3 bars, the temperature 50° C.

The ultrafiltration is followed by a diafiltration when the retentate attains a dry matter content of 130 g/l. The diafiltration degree employed is 1.5.

The permeate is then cooled, stored in a vessel of 60 m³, concentrated up to a concentration of about 350 g protein hydrolysate per litre pasteurized at 95° C., and the concentrate spray dried with air at an inlet temperature 180° C. The thus obtained product has the following physiochemical characteristics (in g/100 g).

| Dry extract | 96.5 | |
|---|---|---|
| Total Nitrogen content (Kjeldahl) | 12.4 | |
| Content of N in the form of free amino groups[1] | 2.6 ±0.5 | |
| Total content of N in NH or NH₂ form | 12.3 ±0.8 | |
| Proteins[2] | 80.3 ± 5 | g/100 g |
| Lipids | <0.5 | g/100 g |
| Glucides | <2.0 | g/100 g |
| Lactose | <2.0 | g/100 g |
| Solubility | 99.8% | |
| pH | 7 ± 0.4 | |
| Composition in Amino Acids (in g/100 g) | | |
| Lysine | 11.1 | |
| Histidine | 1.97 | |
| Arginine | 2.34 | |
| Aspartic acid | 12.6 | |
| Threonine | 4.9 | |
| Serine | 3.6 | |
| Glutamic acid | 17.5 | |
| Proline | 5.5 | |
| Glycine | 1.7 | |
| Alanine | 4.7 | |
| Cystine | 2.22 | |
| Valine | 4.3 | |
| Methionine | 1.76 | |
| Isoleucine | 5.2 | |
| Leucine | 11.5 | |
| Tyrosine | 3.3 | |
| Phenylalanine | 3.45 | |
| Tryptophan | 2.3 | |

| Distribution of molecular weight in % | |
|---|---|
| MW > 5000 | 0 |
| 1400 < MW < 5000 | 26.25 |
| MW < 1400 | 73.30 |
| Total content of free amino acids: | |
| 4.6 g / 100 g powder | |
| Degree of Hydrolysis | |
| Effective: | =30.70 |
| Apparent: | =28.60 |

(1) by standard method, employing 2,4,6-trinitrobenzene sulfonic acid as reactant and detection at 420 nm.
(2) calculated by multiplying the total nitrogen content determined according to Kjeldahl with the factor 6.5.

EXAMPLE 23

Liquid Formulation for Adults

| Per 100 ml | | |
|---|---|---|
| hydrolyzed proteins (1:1:1 hydrolysate mixture according to Example 22, supplemented with threonine) | 4.40 | g |
| fat | 2.58 | g |
| carbohydrates | 19.0 | g |
| energy | 120 | Kcal |
| Minerals/trace elements per 1500 ml | | |
| Sodium | 1000 | mg |
| Potassium | 2500 | mg |
| Calcium | 800 | mg |
| Magnesium | 300 | mg |
| Phosphorus | 800 | mg |
| Chloride | 3000 | mg |
| Iron | 15 | mg |
| Copper | 1.5 | mg |
| Manganese | 3.0 | mg |
| Zinc | 15 | mg |
| Fluoride | 2.0 | mg |
| Iodide | 150 | mg |
| Chromium | 50 | mcg |
| Molybdenum | 75 | mcg |
| Vitamins per 1500 ml | | |
| Vit A | 1.0 | mg |
| Vit B1 | 1.5 | mg |
| Vit B2 | 1.7 | mg |
| Vit B6 | 2.0 | mg |
| Vit B12 | 3.0 | mcg |
| Vit C | 60.0 | mg |
| Vit D3 | 5.0 | mg |
| Vit E | 10.0 | mg |
| Vit K1 | 80.0 | mcg |
| Niacinamide | 19.0 | mg |
| Pantothenic Acid | 6.0 | mg |
| Folacin | 0.2 | mg |
| Biotin | 75.0 | mcg |
| Choline | 200.0 | mg |
| L-Carnitine | 300.0 | mg |

EXAMPLE 24

Formulation for Infants

| per 100 g: | | |
|---|---|---|
| Hydrolyzed proteins * | 13.4 | g |
| Fat | 20.2 | g |
| Carbohydrates | 58.1 | g |

-continued

| | | |
|---|---|---|
| Minerals | 2.8 g | |
| Caloric organic substance | 0.7 g | |
| Humidity (water) | 4.8 g | |
| Minerals: | | |
| Calcium | 300 mg | |
| Phosphorus | 200 mg | |
| Magnesium | 40 mg | |
| Iron | 5.2 mg | |
| Iodide | 30 mcg | |
| Zinc | 3.6 mg | |
| Copper | 300 mcg | |
| Manganese | 60 mcg | |
| Potassium | 590 mg | |
| Chloride | 390 mg | |
| Selenium | 10 mg | |
| Vitamins: | | |
| Vit A | 450 mcg | |
| Vit D3 | 10 mcg | |
| Vit K1 | 21.8 mcg | |
| Vit E | 4 mg | |
| Vit C | 45 mg | |
| Vit B1 | 300 mcg | |
| Vit B2 | 400 mcg | |
| Vit B6 | 300 mcg | |
| Vit B12 | 0.8 mcg | |
| Vit PP | 5 MG | |
| Folic Acid | 50 mcg | |
| Pantothenic Acid | 2 mg | |
| Biotin | 8.2 mcg | |
| Inositol | 21.8 mg | |
| L-Carnitine | 7 mg | |

\* (the 60:40 mixture of selected whey protein hydrolysate with the rennet casein hydrolysate according to Example 22).

---

We claim:

1. A protein hydrolysate comprising a whey protein hydrolysate obtainable by subjecting a whey protein fraction which is substantially free of proteins having a molecular weight of more than 60,000 to the process comprising the steps of:
   (a) heating a solution of said whey protein fraction in water to 43°±4° C. and subjecting said solution to pepsin prehydrolysis at pH between 2.0 and 3.0;
   (b) adjusting the pH of the solution of step a) at a temperature in the range of from 35° to 50° to a pH between 7.0 and 9.0 and submitting said solution to an enzymatic trypsin-chymotrypsin hydrolysis in the presence of a cationic serine endoprotease type 2 elastase; and
   (c) pasteurizing the solution of step b), subjecting said solution to an ultrafiltration, and drying the resulting permeate;
in admixture with a hydrolysate of casein of which the glycoprotein fraction has been eliminated.

2. The protein hydrolysate of claim 1, wherein the whey protein fraction is pasteurized prior to step a).

3. The protein hydrolysate of claim 1, wherein the whey protein fraction is delactosed prior to step a).

4. The protein hydrolysate of claim 1 wherein the whey protein hydrolysate contains from 40 to 60% by weight of its amino acids in the form of oligopeptides of from 4 to 10 amino acids.

5. The protein hydrolysate of claim 1, comprising at least 45% by weight of its amino acids in the form of di- to octapeptides.

6. The protein hydrolysate of claim 1, comprising from 70 to 90% by weight of its amino acids in the form of di- to octapeptides.

7. The protein hydrolysate of claim 6 produced by employing the starting materials a) whey protein substantially free of proteins having molecular weight of more than 60,000 and b) casein of which the glycoprotein fraction has been eliminated in a weight ratio a):b) in the range of from 4:1 to 1:1.

8. The protein hydrolysate of claim 7, wherein the amino acids of said protein hydrolysate have a threonine content of not more than 4.8% by weight.

9. The protein hydrolysate of claim 8, wherein the amino acids of said protein hydrolysate have a threonine content in the range of from 3.9 to 4.8% by weight.

10. The protein hydrolysate of claim 1, further comprising a hydrolysate of soy protein.

11. The protein hydrolysate of claim 10, wherein the whey protein hydrolysate is substantially free of macrolipids.

12. The protein hydrolysate of claim 10, wherein the soy protein is cleared of phytate and phenolic compounds.

13. The protein hydrolysate of claim 10 having a lysine-:arginine weight ratio of less than 2.

14. The protein hydrolysate of claim 13, wherein the lysine:arginine weight ratio is in the range of from 1.35 to 1.75.

15. The protein hydrolysate of claim 14, wherein the lysine:arginine weight ratio is in the range of from 1.35 to 1.6.

16. The protein hydrolysate of claim 10, wherein the amino acids in said protein hydrolysate have a content of sulfur-containing amino acids of less than 3.5% by weight.

17. The protein hydrolysate of claim 16, wherein the content of sulfur-containing amino acids is less than 3% by weight.

18. The protein hydrolysate of claim 17, wherein the content of sulfur-containing amino acids is in the range of from 2.5 to 2.7% by weight.

19. A nutritional composition comprising the protein hydrolysate of claim 1.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO

```
( v i ) ORIGINAL SOURCE:
        ( A ) ORGANISM: Synthetic ( i x ) FEATURE:
        ( A ) NAME/KEY: Modified-site
        ( B ) LOCATION: 1
        ( D ) OTHER INFORMATION: /label=1a
              / note= "glutaryl derivative"

( i x ) FEATURE:
        ( A ) NAME/KEY: Modified-site
        ( B ) LOCATION: 4
        ( D ) OTHER INFORMATION: /label=1b
              / note= "-p-nitro-anilide derivative"

( x i ) SEQUENCE DESCRIPTION: SEQ ID NO:1:

Ala  Ala  Pro  Leu
    1

( 2 ) INFORMATION FOR SEQ ID NO:2:

( i ) SEQUENCE CHARACTERISTICS:
          ( A ) LENGTH: 4 amino acids
          ( B ) TYPE: amino acid
          ( C ) STRANDEDNESS: single
          ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
            ( A ) ORGANISM: Synthetic ( i x ) FEATURE:
            ( A ) NAME/KEY: Modified-site
            ( B ) LOCATION: 1
            ( D ) OTHER INFORMATION: /label=2a
                  / note= "succinyl derivative"

( i x ) FEATURE:
            ( A ) NAME/KEY: Modified-site
            ( B ) LOCATION: 4
            ( D ) OTHER INFORMATION: /label=2b
                  / note= "-p-nitro-anilide derivative"

( x i ) SEQUENCE DESCRIPTION: SEQ ID NO:2:

Ala  Ala  Pro  Met
        1
```